United States Patent [19]

Reti et al.

[11] Patent Number: 4,610,790
[45] Date of Patent: Sep. 9, 1986

[54] PROCESS AND SYSTEM FOR PRODUCING STERILE WATER AND STERILE AQUEOUS SOLUTIONS

[75] Inventors: Adrian R. Reti, Belmont; James A. Benn, Lexington, both of Mass.

[73] Assignee: Sterimatics Company Limited Partnership, Bedford, Mass.

[21] Appl. No.: 578,950

[22] Filed: Feb. 10, 1984

[51] Int. Cl.$^4$ .............................................. B01D 13/00
[52] U.S. Cl. ................................... 210/636; 210/641; 210/651; 210/259; 210/433.2
[58] Field of Search .............. 210/641, 651, 186, 259, 210/638, 321.1, 321.3, 433.2, 636

[56] References Cited

U.S. PATENT DOCUMENTS

| | | | |
|---|---|---|---|
| 3,352,779 | 11/1967 | Austin et al. | 210/646 |
| 3,774,763 | 11/1973 | Yall et al. | 210/259 X |
| 3,836,458 | 9/1974 | Wallis et al. | 210/259 X |
| 4,072,610 | 2/1978 | Gow et al. | 210/259 X |
| 4,342,651 | 8/1982 | Ahrehs | 210/259 X |
| 4,360,435 | 11/1982 | Bellamy et al. | 210/636 |

OTHER PUBLICATIONS

Amicon Selection Guide and Catalog, 3 pages, received in PTD 12-8-78.

Devaney, Defensive Publication, T921,001, published 4-2-74.

Primary Examiner—Frank Spear
Attorney, Agent, or Firm—Andrew T. Karnakis; Paul J. Cook

[57] ABSTRACT

Water substantially free of pyrogens and microorganisms that meets the requirements of United States Pharmacopoeia Standard USP XX Water for Injection is produced by processing drinking quality water through a filtration step adapted to remove organic contaminants and impurities that degrade downstream seperation membranes, a reverse osmosis step to remove dissolved solids, pyrogens, microorganisms and chemical contamination, a deionization step to further remove dissolved solids, and an ultrafiltration step to remove pyrogens. A sterile filter to remove microorganisms increases the water quality to USP XX Sterile Water for Injection. Means are provided to periodically remove accumulated chemical contaminants, pyrogens and microorganisms from the reverse osmosis apparatus, the deionization apparatus and the ultrafiltration apparatus. The sterile water can be admixed with a sterile concentrate composition to produce a sterile dilute solution that can be packaged under sterile conditions.

30 Claims, 2 Drawing Figures

PROCESS AND SYSTEM FOR PRODUCING STERILE WATER AND STERILE AQUEOUS SOLUTIONS

BACKGROUND OF THE INVENTION

This invention relates to the method and apparatus for producing sterile water or a sterile aqueous solution for biological and medical uses. More particularly, this invention relates to a method and apparatus for producing sterile aqueous solutions sufficiently low in bacteria and pyrogen concentration to permit their administration directly to a patient.

Prior to the present invention, sterile therapeutic liquid compositions have been stored in a hermetically sealed container, typically a thermoplastic flexible, transparent container. The liquid compositions which are packaged and subsequently administered to the patient include intravaneous solutions, peritoneal dialysis solutions, irrigation solutions of the like which contain amino acids, sugars such as dextrose or glucose or minerals including electrolytes, vitamins or mixtures thereof. Hermetically sealed containers for these liquid compositions having the correct dilution commonly are prepared at a centralized location wherein sterility can be carefully controlled to assure that the therapeutic preparations are sufficiently low in bacteria and pyrogens that they can be administered to a patient safely. However this procedure is expensive since it involves the shipment of large volumes of water to locations of use as well as high storage costs at the location of use. In addition, the shelf life of these preparations is limited, typically 18 months to two years so that if they are not used, they must be discarded and replaced.

In order to overcome these disadvantages inherent in preparing the solutions at a centralized location, it has been proposed to prepare them at the location of use on an as-needed basis.

Conventional water purification systems employing well known technologies such as reverse osmosis, deionization and ultrafiltration are capable of producing chemically and biologically pure water for short periods of time. Generally, when these systems are run continuously they will maintain low levels of bacteria and pyrogens for up to about two weeks. After that time, colonies of biologically active materials such as bacteria, yeast and mold will begin to multiply within the system is unacceptably high amounts leading to biologic contamination of the normally pure water produced by these systems.

Some conventional systems regain their capacity to produce biologically pure water by rinsing of the systems with sanitizing agents such as formalin or chlorine which kill all biologic contaminants. While these sanitizing agents perform their function well, they are highly toxic to humans, are difficult to rinse out of the purification system and may be accidently introduced into the water to be purified thereby increasing the risk to the patient.

Another method for insuring biologic purity of water treated with a membrane filter systems is to treat the water with a second process which insures the removal of all living organisms. One such method is to heat the purified water with a pasteurization process. Another method is to pass the purified water through a filter that is capable of filtering from the water all biologically active material. However, both of these processes require that the initial filtration treatment reduces the bacterial contamination to less than about 50 colony forming units per ml. of water. At these levels of contamination, chemical sanitization agents are still currently required.

It has been proposed in U.S. Pat. No. 3,578,774 to provide a sterile urological irrigating liquid composition by passing the liquid composition continuously through a filter designed for removing bacteria. However, this device requires an on site source of nonpyrogenic liquid. It has also been proposed in U.S. Pat. No. 4,253,457 to prepare such irrigation solutions on site by utilizing a combination of a reverse osmosis unit for removing pyrogens, a deionization unit for removing dissolved solids and a filter for removing bacterial in order to produce pyrogen free, bacteria free solution that can be administered directly to the patient. However, this system is limited since there is no way to determine whether or not the reverse osmosis system has failed during use and there is no means for removing pyrogens from the liquid should the reverse osmosis unit fail. In addition, the system requires chemical sanitization and cleaning; thereby increasing risk to the patient. Neither of the means disclosed in U.S. Pat. Nos. 3,578,774 or 4,253,457 is capable of producing water that meets the USP XX standards for water for injection or for irrigation. Accordingly, it would be desirable to provide a means for producing pyrogen free, bacteria free water on site having improved safety over the system disclosed in U.S. Pat. No. 4,253,457 and which can be utilized repeatedly over extended periods so that a wide variety of sterile liquid compositions can be provided on site.

British Pat. Nos. 1,450,030 and 2,034,584 also disclose means for providing pyrogen free and bacteria free aqueous solution at the site of use of the solutions. However, each of these systems relies upon the use of chemical sterilization such as with formalin to sanatize the equipment and heat sterilization wherein the water used to form the aqueous solution is heated to a temperature, typically 150° C. to 160° C. The use of chemical sanitization is undesirable even though it is an effective means for killing microorganisms because it also introduces harmful impurities into the system which can accidently be administered to the patient. Furthermore, heat sterilization of the water used to form the aqueous solution is undesirable since power requirements are high, the heated water can burn the patient if it is not cooled properly and the heat sterilization of the water can introduce air into the system which can accidently be transmitted to the patient.

Accordingly, it would be desirable to provide a means for producing water which is essentially pyrogen free and free of microorganisms which eliminates the need for chemical sanitization and eliminates the need for heating the water to be used to form the aqueous solution above normal body temperature. Furthermore, it would be desirable to provide such a system which can be used at the site where the aqueous solutions produced are administered to a patient. Furthermore it would be desirable to provide such a system which can be sanitized without the need for chemical sanitization or heat pasteurization of the aqueous solution so that it can be used on site over an extended period of time.

SUMMARY OF THE INVENTION

In accordance with this invention, a process and apparatus are provided for producing water that can be utilized in aqueous solutions that are substantially free of pyrogens and microorganisms. The water produced by the invention meets the USP XX Water for Injection or Sterile Water for Injection standards. Drinking grade water is passed through a preliminary filter step, a reverse osmosis system, a deionization system and an ultrafiltration system to produce water which is substantially free of pyrogens and low in microorganisms. The water thus produced can then be mixed with a concentrate to form a dilute solution which then passes through a sterilizing filter so that it can be administered to a patient. The dilute solution, after being passed through the filter that retain microorganisms, is collected in a sterile container which can be stored or the solution can be administered directly to a patient. The aqueous solution collected can be stored in bulk or stored in sealed sterile containers housing a unit dosage form of the solution. The system is provided with means for pasteurizing the mechanical components in the system and for flushing it periodically to remove any pyrogens or microorganisms which have been retained therein during purification of incoming water or have grown in the system. Safety features are provided to assure that the reverse osmosis, the deionization, and the sterilizing filtration steps are functioning properly.

DESCRIPTION OF SPECIFIC EMBODIMENTS

In accordance with this invention, purified water which meets the USP XX Water for Injection standard is produced by subjecting drinking quality water to reverse osmosis deionization and lastly ultrafiltration. The USP XX Standard for Water for Injection is published in *Pharmacopoeial Forum,* The United States Pharmacopioial Convention Inc., pages 3012–3020, May–June, 1983. The standard includes a pyrogen content of less than 0.25 USP Endotoxin Units per ml. A filtration step precedes the reverse osmosis system to remove organics and any impurities such as chlorine in the water which may damage the membranes used in the reverse osmosis step. The reverse osmosis system and the ultrafiltration system function remove microorganisms and pyrogens from the water. In addition, the reverse osmosis module removes the bulk of the dissolved ionic contaminants and some other non-ionic dissolved solids including colloids, macromolecules and particulates thereby significantly reducing the requirements on the downstream deionization step. The deionization system functions to remove dissolved solids from the water. The ultrafiltration system provides a means for removing pyrogens from the water which is capable also of being flushed with heated water to remove accumulated pyrogens and microorganisms from the water purification system. Heating means are provided which heats water passing through the system to a temperature between about 60° C. and about 95° C., preferably between about 75° C. and about 85° C. so that the heated water can be used to flush the membranes in the deionization and ultrafiltration step as well as the tubing connecting these steps so that they can be flushed periodically. In another alternative, heating means can be provided to heat water up to about 120° C. in order to sterilize the ultrafiltration apparatus and apparatus downstream of the ultrafiltration apparatus wherein the sterilization water is not used to form the injection grade water. Alternatively, flushing with the water heated to between about 60° C. and 95° C. can also include the reverse osmosis apparatus and the associated tubing. In addition, the system is provided with valving so that connectors to the overall system can be washed periodically with the heated water to remove accumulated pyrogens or microorganisms. The connectors are adapted to be connected with containers for the final sterilized aqueous product produced with the purified water and concentrate passing through the system. Means are also provided for periodically washing the reverse osmosis membranes free of accumulated impurities by means of pumps adapted to pass water under pressure across the surfaces of the membranes and then to a drain. In any case the combination of the above filtration steps all act to produce water that has less than 50 colony forming units per ml of water to be introduced to the sterilizing filter where the rest of the microbiological components are removed.

Figure 1:
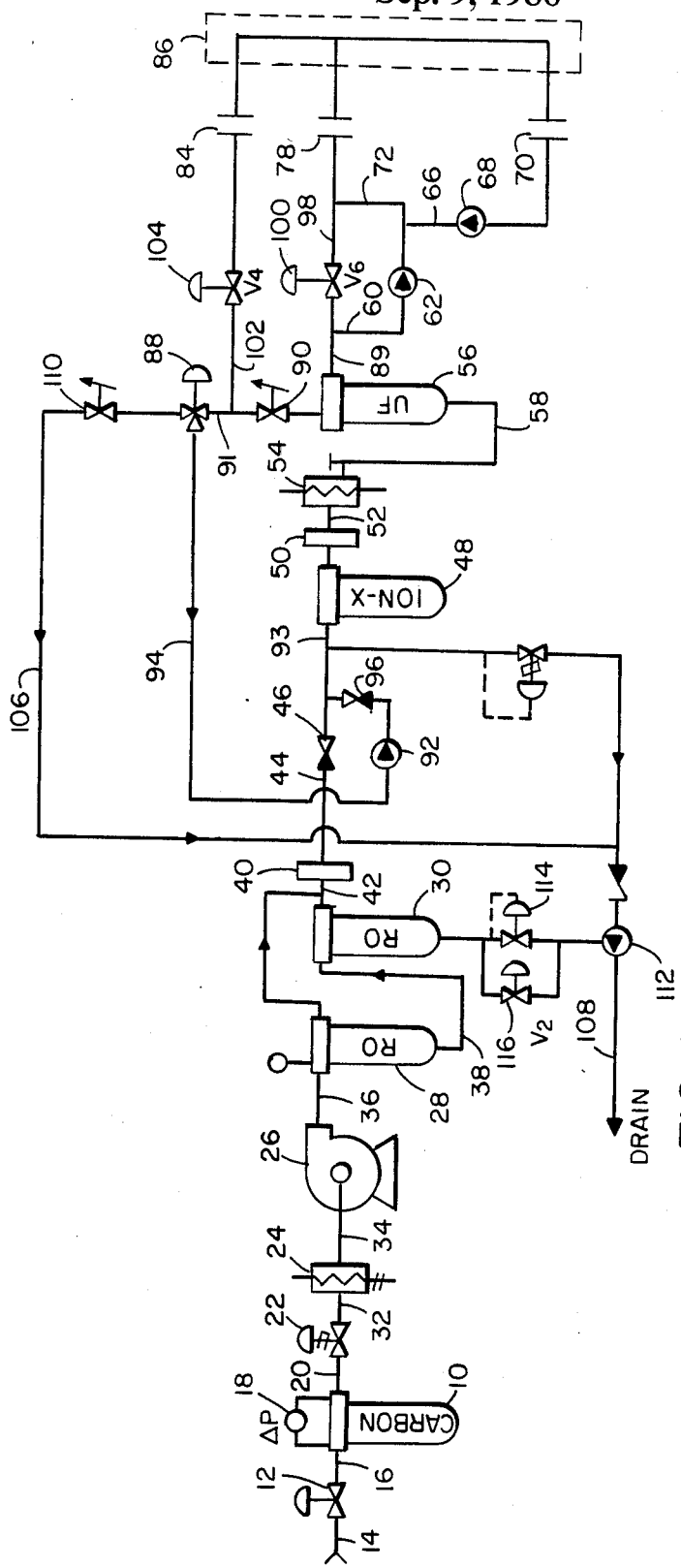
FIG. 1 is a schematic view of the process and apparatus of this invention.

Referring to FIG. 1, the system utilizing the present invention includes a first filtration step 10 which contains a filtration medium such as activated carbon adapted to remove organics and impurities such as dissolved chlorine which would damage some membranes utilized in downstream steps. When the membranes utilized in the downstream steps are resistant to normal impurities in water such as dissolved chlorine, the filtration step 10 need not be used. A valve 12 permits water to enter the system through line 14 and thence through line 16 to filtration step 10. Filtration step 10 is provided with a pressure gauge 18 which shows that filtration step 10 has become clogged when the pressure across the filtration bed exceeds a predetermined standard pressure. Water exits filtration step 10 through line 20, conductivity meter 24 and is pumped by means of pump 26 into reverse osmosis cartridges 28 and 30. The water passes through line 32, 34, 36 and 38 when the system of this invention functions to purify the incoming water. If desired, a plurality of reverse osmosis cartridges can be arranged so that the incoming water passes through them in series. This arrangement further purifies the incoming water so that the purification requirements on the downstream deionization step is materially reduced. In a typical mode of operation, about 33% of the water exits cartridge 30 through line 44 while about 66% of the water is drained through line 108. A conductivity meter 40 also is provided so that, in conjunction with conductivity meter 24, the efficiency of the reverse osmosis cartridges 28 and 30 can be monitored and the quality of water assured. Typical drinking grade feed water has a conductivity of about 300 micro mhos and a bacteria colony count of 10,000–100,000 CFU. The conductivity of the water exiting cartridge 30 through line 42 typically has a conductivity less than about 50 micro mhos, usually between about 20 to 30 micro mhos. The water exiting conductivity meter 40 through line 44 passes through check valve 46 and thence into deionization unit 48. Conductivity meter 50 is provided to monitor the efficiency of deionization step 48 where the conductivity of the water exiting deionization step 48 typically is about 2 to 1 micro mhos. The water exiting deionization step 48 passes through line 52 and into heater 54 which is not activated when the system is being utilized to produce product water. The water passes into ultrafiltration step 56 through line 58 wherein pyrogens and microorganisms are removed therefrom. In a typical mode of operation, about 90% of the purified water passes through line 98 or line 60 for use herein while about 10% of the purified water is passed through line 106 to drain line 108. When the purified water is being used to prepare solutions for administration to a patient, it is passed through line 60 by means of pump 62 wherein it is mixed with sterilized concentrate free of pyrogens and microorganisms passing through line 66 by means of pump 68. A source of the sterilized concentrate is connected to connector 70 for introduction into the system by means of pump 68. The pumps 62 and 68 are controlled so that the proportion of purified water passing through line 60 to the concentrate passing through line 66 is such as to produce the desired dilution of concentrate in line 72 which is delivered to a sterile container 74 for the diluted solution 76. The diluted solution passes through connector 78 and filter 80 such as a 0.22 micron filter within housing 82 which is adapted to retain microorganisms (see FIG. 2). Connector 70, 78 and 84 are covered by cap 86 when either the system is not in use or when it is being cleaned internally with heated water.

When it is desired to cleanse the system of accumulated microorganisms and pyrogens, heater 54 is activated in order to heat water passing therethrough to a temperature between about 65° C. and about 95° C., preferably between about 75° C. and 85° C. As noted above heating means and water circulation means can be provided to sanitize the ultrafiltration apparatus and apparatus downstream of the ultrafiltration apparatus with water heated up to about 120° C., if desired. The heated water passes from heater 54 into ultrafiltration step 56 where about 50% of the water passes across the membrane and exits through valve 90 while the remaining 50% passes through connector 70, 78 and 84. These two water streams are recombined and are recirculated through ion exchange step 48 and ultrafiltration step 56. After the desired heat sanitization is completed valve 88 is controlled so that the heated water passes to drain through lines 106 and 108. By operating in this manner, the deionizer 48 and ultrafiltration step 56 and the associated tubing and membranes are cleared of any microorganisms or pyrogens which may have accumulated therein as well as organic products of thermal degradation of the ion exchange resin, if any. The recirculation of water not only heats to sanitize the system but washes bacterial contaminates onto the ultrafiltration membrane where they are trapped. A portion of the heated water passes through lines 60 and 98 when valve 100 is open and pump 62 and pump 68 are activated so as to clean the connectors 70, 78 and 84 when cap 86 is in place. Cap 86 permits the heated water to enter the connectors and to sterilize the interior of the cap 86 as well as the connectors 70, 78 and 84 and to pass through line 102 when valve 104 is open. The membranes within deionization step 48 and ultrafiltration step 56 also can be washed with the heated water so as to carry any trapped contaminates on the membranes therein to the line 106 and the drain line 108 when valve 110 is open. Similarly, the trapped contaminants on the membranes in reverse osmosis steps 28 and 30 can be flushed by activating pump 26 and opening valve 116 and venturi 112 in order to flush contaminated water through drain line 108.

Table I provides a ready reference to typical operations which can be conducted with the system shown in FIG. I to assure the production of USP XX water for injection over extended time periods at any site where drinking water is available.

TABLE I

| Valves: | | |
|---|---|---|
| Reference | Description | Deactivated State |
| 12 | Inlet Valve | Closed |
| 116 | RO Flush Valve | Closed |
| 88 | UF Recirculate/Drain | Recirculate |
| 104 | Outlet Recirculate | Closed |
| 100 | Water Delivery Valve | Closed |

| Motorized Pumps: | |
|---|---|
| Reference | Description |
| 26 | RO Pump |
| 92 | Recirculation Pump |
| 62 | Sterilized Water Pump |
| 68 | Concentrate Pump |

| Heaters: | |
|---|---|
| Reference | Description |
| 54 | Sanitization Heater |

| | Steps: | | | | | | | | |
|---|---|---|---|---|---|---|---|---|---|
| Name | 12 | 116 | 88 | 104 | 100 | 26 | 92 | 54 | 62 | 68 |
| 1-RO Flush | O | O | R | S | S | P | | | | |
| 2-Sanitize Heat | S | S | R | O | O | | P | H | P | P |
| 3-Sanitize Flush | O | S | D | O | O | P | | | P | P |
| 4-Cooldown | S | S | R | S | S | | | | | |
| 5-Standby | S | S | R | S | S | | | | | |
| 6-System Flush | O | S | D | O | O | P | | | P | P |
| 7-Ready | O | S | D | S | S | P | | | | |
| 8-Deliver Water | O | S | D | S | O | P | | | | |
| 9-Seal Bags | O | S | D | S | S | P | | | | |
| 10-Integrety Test | O | S | D | S | S | P | | | | |
| 11-System Fill | O | S | D | O | O | | | | | |
| 12-Depressurize | S | O | D | O | O | | | | | |
| 13-Deliver Mixture or Fill Bags | O | S | D | S | S | P | | | P | P |

O — Open
S — Shut
R — Recirculate
D — Drain
P — Pumping
H — Heating

The operations include water delivery, flushing, sanitization, bag filling with sanitized water or aqueous solution. In step 1, the reverse osmosis membrane is flushed. In step 2, the ultrafiltration and deionization steps are sanitized with heated water. In step 3, air is flushed from the system. In steps 4 and 5, the system is prepared for actual use. In step 6, the system is flushed for a short time before the system is ready (step 7) for use. In step 8, sanitized water is delivered by the system. In step 13 dilute mixtures of concentrate and sanitized water are delivered to sterile containers. In step 9, the containers, eg. bags are sealed. In step 10, the sterilizing filters associated with the bags are tested for integrity to assure that the fluid entering the bags is in fact sterile. In step 11, the system is provided with water under pressure. In step 12, the system is depressurized to allow for maintenance activities. Thus, the system of this invention can be used (1) to deliver USP XX grade water for injection, (2) to deliver an aqueous composition formed of the pure water and a concentrate or (3) to provide sealed sterile containers containing a sterile aqueous composition to be administered to a patient.

During flushing of the reverse osmosis steps 28-30, 100% of the flushing water passes to drain through line 108. This step normally is done just prior to use for a short time period, 5 minutes or less so as to remove accumulated contaminants in this step as well as in associated tubing. Flushing of the deionization step 48 and ultrafiltration step 56 also is effected for a short time period for the same purpose just prior to use of the system so that 100% of the water passes through drain line 108. The tubing associated with the ultrafiltration step 56 and with the deionization step 48 also can be cleaned by recirculating water through lines 91, 94, 93 and 58 without activating heater 54 so that accumlated pyrogens and microorganisms are deposited on the membranes in these steps. During recirculation and/or flushing, about 50% of the water passes through the ultrafiltration membrane and line 89 while the remaining water passes across the membrane and through line 91. During flushing, recirculation and heat sanitization, cap 86 is maintained in place so that circulating water can clean and sanitize connectors 70, 78 and 84.

Figure 2:
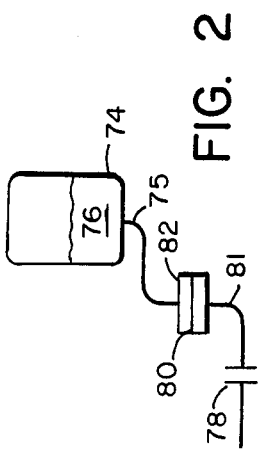
FIG. 2 illustrates the container utilized with the present invention.

Referring to FIG. 2, the package for the dilute solution 76 includes a sterile container 74 and tubing 75 which have been sterilized by any conventional means such as by ionizing radiation, ethylene oxide or heat. The container 74 and tubing 75 are formed integrally with filter housing 82 containing filter 80 which also are pre-sterilized. Tubing 81 is attached to housing 82 and is adapted to fit connector 78 so that the dilute solution produced by the system of this invention can be delivered into container 74 through filter 80 which is adapted to retain microorganisms. A suitable filter 80 and conventional filter such as those having a pore size not greater than 0.22 microns is available from Millipore Corporation of Bedford, Mass. The housing 82 can be connected to a plurality of bags 74 with appropriate tubing connections so that all water or aqueous solution directed to each bag passes through filter 80. The container 74 usually is a flexible transparent bag formed of plastic composition which is moisture proof and impermeable to microorganisms such as polyvinylchloride, polyethylene, polypropylene, polyethylene terephthalate or the like. The tube 75 can be sealed after the bag 74 is filled so that microorganisms or other contaminants do not enter the bag prior to use of the filled bag.

The membrane filter, 80, is tested upon manufacture, to ensure that it will perform its sterilizing function. When the system of this invention is used to fill bags, as shown in FIG. 2, at the end of the bag filling sequence, the filter is tested to determine that it still retains the capacity to perform its sterilizing function. This test acts as a quality assurance test to prove that the bags have indeed been filled with solution that has been sterilized.

The test that is performed is to assure that all the pores in the filter are small enough to trap and filter out bacteria from the fluid flowing through the filter, e.g., 0.22 microns.

The test can be performed in several different ways. A preferable test is to inject air upstream of the filter to be tested, at a pressure of about 20 to 40 psi, and then seal off the upstream side of the membrane, and measure the rate of decay of the pressure as air diffuses across the membrane. The wetted surface of the filter will sustain the pressure due to water surface tension acting across the pores of the membrane. Air diffusion will take place at a slow rate, however, across the membrane. This diffusion rate is proportional to the area and thickness of the membrane, and can be expected to be within known bounds for specific filters. Gas flow greater than these limits is due to bulk flow of gas passing through larger pores or damaged areas of the filter either of which may allow bacteria to pass through it. Thus, membranes that have been damaged, and did not perform their sterilizing function, can be discovered.

It is to be understood that the above description of FIGS. 1 and 2 describe the preferred embodiment of this invention. The filtration step 10, reverse osmosis steps 28-30 and deionization step 48 can be in any sequence. For example, if the incoming impure water contains no chlorine or if the reverse osmosis membrane is chlorine resistant, reverse osmosis steps 28-30 can precede filtration step 10. However, the ultrfiltration step is utilized downstream of the reverse osmosis and deionization steps in order to maximize removal of pyrogens in the incoming water or produced within the water purification system. The system functions set forth in Table I can be controlled in any conventional manner such as by utilizing a microprocessor which is capable of controlling the system functions in response to pre-set time controls and in response to measured system conditions. Such system conditions include the physical characteristics of the water being processed such as conductivity and pressure and system conditions such as integrity of membrane filter 80 as well as verification of compliance with the pre-set time-temperature heat sanitization and flushing cycles.

We claim:

1. A process for producing water substantially free of pyrogens to produce USP XX grade water for injection or irrigation solutions which comprises passing drinking quality water through a water purification system comprising:
    (a) a filtration step to remove organic impurities;
    (b) a reverse osmosis separation step to remove dissolved solids or ions, pyrogens and microorganisms from said water;
    (c) a deionization step to remove ions from said water and to increase the electrical resistance of said water;
    (d) an ultrafiltration step downstream of steps (a), (b) and (c) thereby to remove pyrogens from said water; and
    (e) periodically washing ion exchange means in the deionization step for removing ions from said water and a membrane utilized in the ultrafiltration step with water heated to a temperature to sterilize microorganisms in said deionization and ultrafiltration steps and to remove impurities accumulated in said deionization step and said ultrafiltration step while avoiding washing steps (a) and (b) with said heated water.

2. A process for producing water substantially free of pyrogens and microorganisms to produce sterile USP XX grade sterile water for injection which comprises passing drinking quality water through a water purification system comprising:
    (a) a filtration step to remove organic impurities;
    (b) a reverse osmosis separation step to remove dissolved solids or ions, pyrogens and microorganisms from said water;
    (c) a deionization step to remove ions from said water and to increase the resistance of said water;
    (d) an ultrafiltration step subsequent to steps (a), (b) and (c) thereby to remove pyrogens from said water;
    (e) a membrane filter step capable of retaining microorganisms; and
    (f) periodically washing ion exchange means in the deionization step for removing ions from said water and a membrane utilized in the ultrafiltration step with water heated to a temperature to sterilize microorganisms in said deionization and ultrafiltration steps and to remove impurities accumulated in said deionization step and said ultrafiltration step while avoiding washing steps (a) and (b) with said heated water.

3. The process of claim 1 wherein the drinking quality water is passed sequentially through steps (a), (b), (c) and (d).

4. The process of claim 2 wherein the drinking quality water is passed sequentially through steps (a), (b), (c), (d), and (e).

5. The process of any one of claims 1, 2, 3 or 4 wherein membranes in the reverse osmosis step, the deionization step and the ultrafiltration step are cleaned periodically by being flushed with water in said system.

6. A process for preparing a sterile package containing a sterile dilute aqueous solution formed from sterile USP XX grade water for injection water and irrigation and adapted to be administered to a patient which comprises passing drinking grade water through a water purification system comprising:
   (a) a filtration step to remove organic impurities;
   (b) a reverse osmosis separation step to remove dissolved solids or ions, pyrogens and microorganisms from said water;
   (c) a deionization step to remove ions from said water and to increase the resistance of said water;
   (d) an ultrafiltration step subsequent to steps (a), (b) and (c) thereby to remove pyrogens from said water and produce USP XX grade water for injection or irrigation;
   (e) mixing said sterile water with a sterilized liquid concentrate composition thereby to produce said sterile dilute solution;
   (f) passing said dilute solution through a filter adapted to retain microorganisms into a sterile container; and
   (g) periodically washing ion exchange means in the deionization step for removing ions from said water and a membrane utilized in the ultrafiltration step with water heated to a temperature to sterilize microorganisms in said deionization and ultrafiltration steps and to remove impurities accumulated in the deionization and ultrafiltration steps while avoiding steps (a) and (b) with said heated water.

7. The process of claim 6 wherein the drinking water is passed sequentially through steps (a), (b), (c), (d), (e) and (f).

8. The process of any one of claims 6 or 7 wherein said dilute solution is passed through filtration means adapted to retain microorganisms and then into a plurality of sterile containers.

9. The process of any one of claims 6 or 7 wherein said sterile containers are transparent flexible containers.

10. The process of any one of claims 6 or 7 wherein said filled packages are sealed from the atmosphere after being filled.

11. The process of any one of claims 6 or 7 wherein said sterile containers are transparent flexible containers and the filled packages are sealed from the atmosphere after being filled.

12. A system for producing USP XX grade sterile water for injection from drinking water which comprises
   (a) a filtration means adapted to remove organic impurities from water;
   (b) a reverse osmosis separation means adapted to remove dissolved solids, microorganisms and pyrogens from water;
   (c) deionization means adapted to remove dissolved solids from water;
   (d) ultrafiltration means downstream of steps (a), (b) and (c) adapted to remove pyrogens and microorganisms from water;
   (e) means for passing the drinking grade water through said first filtration means, said reverse osmosis separation means, said deionization means and said ultrafiltration means;
   (f) means for passing heated water periodically through said deionization means and said ultrafiltration means thereby to remove accumulated pyrogens and microorganisms from said system while avoiding washing means (a) and (b) with said heated water; and
   (g) means for passing pressurized water across membranes in said reverse osmosis means to remove accumulated microorganisms from said system.

13. The system of claim 12 wherein said drinking water is passed sequentially through means (a), (b), (c) and (d).

14. A system for preparing a package containing a sterile dilute aqueous solution adapted to be administered to a patient said solution being formed from USP XX grade water for injection or irrigation which comprises
   (a) a filtration means adapted to remove organic impurities from water;
   (b) a reverse osmosis separation means adapted to remove dissolved solids, microorganisms and pyrogens from water;
   (c) deionization means adapted to remove dissolved solids from water;
   (d) ultrafiltration means downstream of steps (a), (b) and (c) adapted to remove pyrogens and microorganisms from water;
   (e) means for passing the drinking grade water through said first filtration means, said reverse osmosis separation means, said deionization means and said ultrafiltration means;
   (f) means for passing heated water periodically through said deionization means and said ultrafiltration means thereby to remove accumulated pyrogens and microorganisms from said system while avoiding washing means (a) and (b) with said heated water; and
   (g) means for passing pressurized water across membranes in said reverse osmosis means to remove accumulated microorganisms from said system.

15. The system of claim 14 wherein said drinking grade water is passed sequentially through means (a), (b), (c) and (d).

16. The system of any one of claims 14 or 15 wherein said dilute solution is passed into a plurality of sterile packages under sterile conditions.

17. The system of any one of claims 14 or 15 wherein said sterile packages are transparent flexible containers.

18. The system of any one of claims 14 or 15 including means for sealing said packages containing said dilute solutions from the atmosphere under sterile conditions.

19. The system of any one of claims 14 or 15 wherein said sterile packages are transparent flexible packages and means are included for sealing said packages containing said dilute solution from the atmosphere under sterile conditions.

20. A process for producing water substantially free of pyrogens to produce USP XX grade water for injection or irrigation solutions which comprises passing drinking quality water through a water purification system comprising:

(a) a filtration step to remove organic impurities;
(b) a reverse osmosis separation step to remove dissolved solids or ions, pyrogens and microorganisms from said water;
(c) a deionization step to remove ions from said water and to increase the electrical resistance of said water;
(d) an ultrafiltration step downstream of steps (a), (b) and (c) thereby to remove pyrogens from said water; and
(e) periodically washing a membrane utilized in the ultrafiltration step with water heated to a temperature to sterilize microorganisms in said systems and to remove impurities accumulated on said membrane while avoiding washing steps (a) and (b) with said heated water.

21. A process for producing water substantially free of pyrogens and microorganisms to produce sterile USP XX grade sterile water for injection which comprises passing drinking quality water through a water purification system comprising:

(a) a filtration step to remove organic impurities;
(b) a reverse osmosis separation step to remove dissolved solids or ions, pyrogens and microorganisms from said water;
(c) a deionization step to remove ions from said water and to increase the resistance of said water;
(d) an ultrafiltration step subsequent to steps (a), (b) and (c) thereby to remove pyrogens from said water;
(e) a membrane filter step capable of retaining microorganisms; and
(f) periodically washing a membrane utilized in the ultrafiltration step with water heated to a temperature to sterilize microorganisms in said systems and to remove impurities accumulated on said membrane while avoiding washing steps (a) and (b) with said heated water.

22. The process of claim 20 wherein the drinking quality water is passed sequentially through steps (a), (b), (c) and (d).

23. The process of claim 21 wherein the drinking quality water is passed sequentially through steps (a), (b), (c), (d), and (e).

24. The process of any one of claims 20, 21, 22 or 23 wherein membranes in the reverse osmosis step, the deionization step and the ultrafiltration step are cleaned periodically by being flushed with water in said system.

25. A process for preparing a sterile package containing a sterile dilute aqueous solution formed from sterile USP XX grade water for injection water and irrigation and adapted to be administered to a patient which comprises passing drinking grade water through a water purification system comprising:

(a) a filtration step to remove organic impurities;
(b) a reverse osmosis separation step to remove dissolved solids or ions, pyrogens and microorganisms from said water;
(c) a deionization step to remove ions from said water and to increase the resistance of said water;
(d) an ultrafiltration step subsequent to steps (a), (b) and (c) thereby to remove pyrogens from said water and produce USP XX grade water for injection or irrigation;
(e) mixing said sterile water with a sterilized liquid concentrate composition thereby to produce said sterile dilute solution;
(f) passing said dilute solution through a filter adapted to retain microorganisms into a sterile container; and
(g) periodically washing ion exchange means in the ultrafiltration step with water heated to a temperature to sterilize microorganisms in said system and to remove impurities accumulated on said membrane while avoiding steps (a) and (b) with said heated water.

26. The process of claim 25 wherein the drinking water is passed sequentially through steps (a), (b), (c), (d), (e) and (f).

27. The process of any one of claims 25 or 26 wherein said dilute solution is passed through filtration means adapted to retain microorganisms and then into a plurality of sterile containers.

28. The process of any one of claims 25 or 26 wherein said sterile containers are transparent flexible containers.

29. The process of any one of claims 25 or 26 wherein said filled packages are sealed from the atmosphere after being filled.

30. The process of any one of claims 25 or 26 wherein said sterile containers are transparent flexible containers and the filled packages are sealed from the atmosphere after being filled.

* * * * *